United States Patent [19]

McCaulley

[11] Patent Number: 5,300,718
[45] Date of Patent: Apr. 5, 1994

[54] OLEFIN CONVERSION PROCESS

[75] Inventor: Michael W. McCaulley, Houston, Tex.

[73] Assignee: Lyondell Petrochemical Company, Houston, Tex.

[21] Appl. No.: 11,126

[22] Filed: Jan. 29, 1993

Related U.S. Application Data

[60] Continuation of Ser. No. 839,656, Feb. 20, 1992, abandoned, which is a division of Ser. No. 750,426, Aug. 19, 1991, Pat. No. 5,120,894, which is a continuation of Ser. No. 246,463, Sep. 19, 1988, abandoned.

[51] Int. Cl.$^5$ .............. C07C 1/00; C07C 2/00; C07C 4/00; C07C 5/00
[52] U.S. Cl. ................... 585/324; 585/646; 585/664
[58] Field of Search ............. 585/324, 664, 646

[56] References Cited

U.S. PATENT DOCUMENTS

| | | | |
|---|---|---|---|
| 3,080,433 | 3/1963 | Hengstebeck | 585/324 |
| 3,240,830 | 3/1966 | Dye | 585/324 |
| 3,658,929 | 4/1972 | Banks | 260/683 |
| 3,776,975 | 12/1973 | Verbrugge et al. | 260/683 |
| 3,786,112 | 1/1974 | Reusser et al. | 260/683 |
| 3,865,751 | 2/1975 | Banks et al. | 252/457 |
| 4,085,158 | 4/1978 | Dixon et al. | 260/680 |
| 4,243,813 | 1/1981 | Malloy et al. | 585/324 |
| 4,575,575 | 3/1986 | Drake et al. | 585/646 |
| 4,605,810 | 8/1986 | Banks | 585/646 |
| 4,609,769 | 9/1986 | Kukes et al. | 565/646 |
| 4,714,788 | 12/1987 | Michaelson et al. | 585/324 |
| 4,835,338 | 5/1989 | Liu | 585/324 |
| 5,026,935 | 6/1991 | Leyshon et al. | 585/324 |
| 5,120,894 | 6/1992 | McCauley | 585/664 |

FOREIGN PATENT DOCUMENTS 213667 9/1984 Fed. Rep. of Germany ...... 585/324

Primary Examiner—Asok Pal
Attorney, Agent, or Firm—Vinson & Elkins

[57] ABSTRACT

Propylene is produced from the disproportionation of impure butene-2 containing oxygenates and butene-1 by treatment with alumina and isomerization of the butene-1 prior to disproportionation with ethylene.

2 Claims, No Drawings

OLEFIN CONVERSION PROCESS

This application is a continuation of application Ser. No. 07/839,656 filed Feb. 20, 1992, now abandoned, which in turn is a divisional application of application Ser. No. 07/750,426 filed Aug. 19, 1991, now U.S. Pat. No. 5,120,894, which in turn is a continuation application of application Ser. No. 07/246,463, filed Sep. 19, 1988, now abandoned.

BACKGROUND OF THE INVENTION

In one aspect, the invention relates to an olefin conversion process. In another respect, the invention relates to the purification of hydrocarbon streams.

Prior to the invention, high purity feeds were required for disproportionation conversion reactions. For the conversion of butene-2 with ethylene to produce propylene, for example, a butene-2 purity in excess of 75% by weight was required, and oxygenates in the feed could not be tolerated. Sources of such a feedstock were quite limited and expensive.

One such source, for example, was an ethylene dimerization unit operated with a nickel octanoate triphenyl phosphate catalyst. With increasing ethylene costs, an alternative, less expensive, butene-2 source was clearly needed.

One such source that was identified was formed by removing the isobutene from a mixed $C_4$ stream by reaction with methanol and the butadiene by absorption with acetonitrile. This stream, however, contained a low level of butene-2, on the order of 15% wt %, and high levels on the order of 0.1 wt % or more, of oxygenates, which are known disproportionation catalyst poisons.

In a preferred embodiment, this invention relates to process modifications made to permit propylene production from this feedstock via disproportionation.

STATEMENT OF THE INVENTION

Use of low purity butene for olefin disproportionation(DP)/conversion/metathesis Use of alumina for purification of butenes, especially butenes for disproportionation feed.

Use of alumina for alcohol, MTBE, various oxygenates and dimethy ether removal from butenes.

Improved disproportionation isomerization catalyst configurations for use with low butene-2 streams.

GENERAL

In disproportionation, the primary reaction is a reaction which can be visualized as comprising the breaking of two existing unsaturated bonds between first and second carbon atoms and between third and fourth carbon atoms, respectively, and the formation of two new unsaturated bonds between said first and third and between said second and fourth carbon atoms. Said first and second carbon atoms and said third and fourth carbon atoms can be in the same or different molecules.

The reaction can be illustrated by the following example illustrating the disproportionation reaction between butene-2 and ethylene to produce propylene:

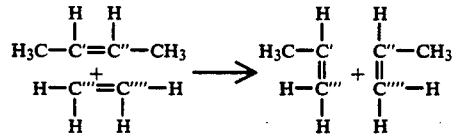

The variety of olefin conversions possible via disproportionation is illustrated by the following reactions:

1. The disproportionation of an acyclic mono or polyene having at least three carbon atoms into other acyclic mono or polyenes of both higher and lower number of carbon atoms.
2. The conversion of an acyclic mono or polyene having three or more carbon atoms and a different acyclic mono or polyene having three or more carbon atoms to produce different acyclic olefins.
3. The conversion of ethylene or an acyclic mono or polyene having three or more carbon atoms and a cyclic mono or cyclic polyene to produce an acyclic polyene having a higher number of carbon atoms than that of any of the starting materials.
4. The conversion of one or more cyclic mono or cyclic polyenes to produce a cyclic polyene having a higher number of carbon atoms than any of the starting materials.
5. The conversion of an acyclic polyene having at least seven carbon atoms and having at least five carbon atoms between any two double bonds to produce acyclic and cyclic mono and polyenes having a lower number of carbon atoms than that of the feed.
6. The conversion of one or more acyclic polyenes having at least three carbon atoms between any two double bonds to produce acyclic and cyclic mono and polyenes generally having both a higher and lower number of carbon atoms than that of the feed material.
7. The conversion of ethylene and an internal acyclic mono or polyene having four or more carbon atoms to produce other olefins having a lower number of carbon atoms than that of the acyclic mono or polyenes, for example.

FEEDSTOCK AND SOURCE

Olefins applicable for use in the process of the invention include acyclic mono and polyenes having at least three carbon atoms per molecule and cycloalkyl and aryl derivatives thereof; cyclic mono and polyenes having at least four carbon atoms per molecule and alkyl and aryl derivatives thereof; mixtures of two or more of the above olefins; and mixtures of ethylene with one or more of the above olefins. Many useful reactions are accomplished with such acyclic olefins having 3-30 carbon atoms per molecule and with such cyclic olefins having 4-30 carbon atoms per molecule.

The preferred feedstock for the disproportionation reaction comprises a 2-olefin, most preferably 2-butene, which is reacted with a 1-olefin, such as 1 butene but preferably ethylene, to produce propylene and optional other olefins. This feedstock is preferably an isomerizate from an isomerization zone in which a 2-olefin precursor, such as 1-butene, is converted to the desired 2-olefin feed for disproportionation; and contains over 90 percent by weight of $C_4$ hydrocarbons. The feed for the isomerization zone is preferably a deoxygenate from an adsorption zone, preferably one which contains a bed of alumina, which has been used with good results. The deoxygenate can contain inerts such as butanes, in rather large amounts, say in the range of from 5 to 50% based on weight. When the invention is used, the amount of 2-olefin in the deoxygenate can be small, say in the range of from 2 to 40% by weight, generally from 5 to 25% by weight. The amount of 2-olefin precursor can be rather large, say in the range of from 15 to 95% by weight, generally from 20 to 80% by weight, since the 2-olefin concentration is increased in the isomerization zone, at the expense of the 2-olefin precursor concentration, which is reduced. An inexpensive feed for the oxygenate adsorption can be formed by the raffinate from an acetonitrile extractive distillation unit, operated under conditions to recover butadiene in the extract. When alumina is used as the adsorbant in the adsorption zone, charge to the ACN extraction can be recovered from an etherification unit, such as for the production of MTBE from isobutylene and methanol, due to the efficacy of alumina for removing alcohols, ethers and oxygenates from the isomerization unit charge stock which can contain in the range of 0.01-3% by weight of such materials, for example. Charge stock for the etherification unit can be the mixed $C_4$ stream from a thermal pyrolyzation unit, for example.

The invention thus makes possible recovering MTBE, butadiene, propylene and butanes from a mixed $C_4$ stream.

DEOXYGENATION OF FEED

The purity of a feed is an important factor in any chemical process in that its effects directly the efficiency or even operabiilty of that process. Olefin disproportionation processes in general require the substantial absence of materials which cause difficulties, for example, by poisioning of the catalyst. Some of these impurities, for example, oxygen and water, are known; others are unknown.

In a preferred embodiment of the invention, the olefin can be treated by passing it through a fixed or fluidized bed of activated alumina or contact can be made by suspending the alumina, by suitable agitation in the vessel containing the olefin to be treated. The contact with the alumina can be either in vapor or liquid phase depending upon the nature of the olefin to be treated but is preferably liquid phase. The time of contact, throughput rate in regard to a fixed bed of alumina, or alumina usage per unit weight olefin, varies greatly with the olefin being treated and the degree of treatment which may be required to bring the olefin into condition for reaction. Because the nature of the impurities removed are not always known, the optimum extent of treatment often can best be determined by trial and error. Usually, impurities will be present at a level in the range of 0.05 to 1 wt %, such as about 0.1 wt %.

Preferably, the treatment with alumina is prior to introduction of the feedstream into the isomerization catalyst bed. In a most preferred embodiment, a fixed bed of alumina is employed, with upflow of the olefin stream. Particles of alumina having a size in the range of 1/16-⅛ inch for example, ⅛ inch will provide results, especially aluminas having a surface area in the range of 200–500 $m^2/g$, for example, about 350 $m^2/g$.

TREATMENT CONDITIONS

Conditions in the alumina bed typically include a pressure in the range of 250–1,000 psig, for example, about 500 psig, a temperature in the range of 40–110 degrees F., for example, abiyt 75 degrees F., and a WHSV in the range of 0.5–10 for example, in the range of 1.05 to 4.5 wt/wt/hr, such as 1.56 wt/wt/hr. the bed can be regenerated by flow of hot inert gas, such as nitrogen at 500 degrees F. For this, the bed must be taken off-line, and thus tandem units are preferred.

ISOMERIZATION CATALYST

A wide variety of isomerization catalysts can be used. Preferred catalysts are those which have little or no polymerization or cracking activity and which are active for isomerization at conditions suitable for obtaining a disproportionated product with the selected disproportionation catalyst. Some examples of suitable isomerization catalysts include supported phosphoric acid, bauxite, alumina supported cobalt oxide or iron oxide or manganese oxide, zinc oxide, supported alkali metal, and the like. Magnesium oxide is preferred.

Magnesia suitable for use in the invention can be any suitably activated material known in the art. The material normally has a surface area of at least 1 $m^2/g$. The magnesia can be naturally occurring, such as the mineral Brucite, or can be synthetically prepared by suitable techniques. Minor amounts of other materials such as silica, alumina, and the like, can be present but the material is principally magnesium oxide generally at least 95% by weight. Depending upon the contacting technique used for the isomerization, the activated magnesia can be in the form of pellets, extrudates, agglomerates, or even a fine powder. Before use in the process, the magnesium oxide is activated in a suitable manner such as by heating in a flowing stream of an oxygen-containing gas for about 1 to about 30 hours at 500 degrees to about 1,500 degrees F., preferably 600 degrees to about 1,000 degrees F. After activation sometimes it is advisable to flush the catalyst with an inert gas to remove any adsorbed oxygen or other gases from the magnesium oxide. The regeneration of spent magnesium oxide isomerization catalyst is generally accomplished by a technique which is similar to the activation of this material. Preferably, the isomerization catalyst is regenerated by combustion with air diluted with nitrogen so as to not exceed a temperature of about 1100 degrees F.

ISOMERIZATION CONDITIONS

When using magnesium oxide, the reaction can be accomplished at temperatures ranging from about 50 degrees to 1,000 degrees F., preferably about 300 degrees to about 900 degrees F., most preferably at a temperature in the range of 525 to 650 degrees F., at any suitable pressure and at residence times or throughout rates which will effect the desired degree of isomerization. Preferred operation is between 550 and 575 degrees F.

DISPROPORTIONATION CATALYST

The disproportionation catalysts which are useful for the present invention are those which have actively for the disproportionation of propylene into ethylene and butenes. Some examples of such catalysts are 1. silica or thoria promoted by an oxide or a compound convertible to the oxide by calcination or sulfide of tungsten or molybdenum or by an oxide or a compound convertible to the oxide by calcination of rhenium or tellurium;
2. alumina promoted with an oxide or compound convertible to an oxide by calcination of molybdenum, tungsten, or rhenium; a sulfide of tungsten or molybdenum; or an alkali metal salt, ammonium salt, alkaline earth metal salt, or bismuth salt of phosphomolybdic acid;

3. one or more of the group aluminum phosphate, zirconium phosphate, calcium phosphate, magnesium phosphate, or titanium phosphate promoted by one or more of a sulfide of molybdenum or tungsten, or an oxide or a compound convertible to the oxide by calcination or molybdenum, tungsten or rhenium or magnesium tungstate or beryllium phosphotungstate; and 4. silica, alumina, aluminum phosphate, zirconium phosphate, calcium phosphate, magnesium phosphate, or titanium phosphate promoted by a hexacarbonyl of molybdenum or tungsten.

The catalysts of (1) are preferred and can be prepared and activated by conventional techniques such as by combining a catalyst grade silica with suitable tungsten molybdenum, rhenium or tellurium compounds by a conventional method such as, for example, impregnation, dry mixing, or coprecipitation. Suitable tungsten and molybdenum compounds include tungsten oxide and molybdenum oxide and compounds convertible to these oxides. The supported oxides are activated by calcining in air and the supported sulfides are activated by heating in an inert atmosphere.

When using a metallic alkali metal treated olefin disproportionation catalyst, a first step in the catalyst preparation comprises associating molybdenum oxide or tungsten oxide or a molybdenum or tungsten compound convertible to the oxide upon calcination with a support such as alumina, silica, or silica-alumina. This first step can be carried out by any suitable means for the preparation of catalysts such as by impregnation, to obtain a composition containing from about 0.1 to about 30, usually 1 to 15, and preferably 5-10 weight percent of molybdenum oxide or tungsten oxide based upon the total catalytic composition. Minor amounts of other materials which are compatible with the olefin reaction can also be present in the catalyst. Some of these are titanic, magnesia, cobalt oxide, and small amounts of inorganic bases such as NaOH, KOH, and the like. Some compositions particularly applicable for use in this invention comprise alumina impregnated with a molybdenum compound and with a small amount of KOH. Such a component is then activated by heating in a stream of air or other oxygen-containing gas for 0.1 to 30 hours at 700 degrees to 1,500 degrees F., preferably 900 degrees to 1,100 degrees F. After such an activation, the oxide composite is flushed with an inert gas such as nitrogen and maintained at such an atmosphere throughout the rest of the preparation until the finished catalyst is utilized in the reaction.

The activated oxide composite is contacted with metallic alkali metal in an amount which ranges from about 0.1 to about 30, preferably 2 to about 10, weight percent based on the total weight of the finished catalyst. In the case of catalysts having a base predominantly silica, the amount of alkali metal preferably is about 0.1 to about 5 weight percent. The contact can be carried out by any suitable means such as by contacting the solid oxide composite with either molten or vaporized alkali metal, such as sodium, for a period of time which may vary from about 1 minute to about 10 hours. This can be accomplished using sodium, for example, by melting sodium and dropping the molten sodium on a molybdena-alumina catalyst or by passing a stream of inert gas such as nitrogen or argon through the molten sodium and then over a bed of the molybdena-alumina. Contact of an alkali metal with the oxide composite generally is exothermic and causes the catalyst to take on a gray to black color.

The alkali metals utilizable in the process are selected from the group consisting of lithium, sodium, potassium, rubiduium, cesium and mixtures thereof. Sodium and potassium are preferred in many instances with sodium being especially desirable.

The finished catalyst can be in the form of powder, or granules as well as in other shapes such as agglomerates, pellets, spheres, extrudates, beads, and depending upon the type of contacting technique which utilizes the catalyst. An examplary catalyst comprises tungsten oxide on crystalline silica, in tablet form with a particle size of 1/16 to ⅛ inches. The amount of tungsten oxide employed can generally range from 1-15% based weight of tungsten oxide and silica, typically about 8%.

DISPROPORTIONATION CONDITIONS

The operating temperature for the process of this invention when using preferred catalysts is broadly in the range of about 400 degrees to 1,100 degrees F. In the process of the invention, pressures are not important but will be in the range of about 0 to 2,000 psig. In the preferred embodiment of the invention, a temperature in the range of 525 to 650 degrees F. is used, typically about 50 –575 degrees F., to reduce pentene-2 production, which is higher at higher temperatures. Preferred pressure is generally in the range of 350–500 psig, typically 425 psig. A ethylene-butene mole ratio of from about 0.5:1 about 1.9:1 can be employed, typically 0.8:1 to 1.3:1. Weight hourly space velocity (based on hydrocarbon charge and total wt of disproportionation catalyst and support), generally ranging from 5 to 50 wt/wt/hr can be used, usually from 10 to 25, with 15.6 a typical example.

CATALYST MIXTURE

In a preferred embodiment of the invention, a mixed bed of isomerization catalyst and disproportionation catalyst forms the reaction zone. When preparing a mixed bed of magnesium oxide and tungsten oxide on silica catalyst, particles of magnesium oxide and particles of the tungsten on silica catalyst of about the same particle size can be blended. Alternatively, both magnesium oxide and the tungsten oxide on silica catalyst can be intimately blended such as by grinding and the powder then formed into other shapes such as pellets, tablets, agglomerates, extrudates, and the like, such that each particle in the catalytic zone comprises an intimate blend of the two catalysts.

The proportion of magnesium oxide to the disporportionation catalyst in the composite catalyst system can vary widely. At least about 0.1 part by weight of magnesium oxide should be present for each part by weight of disproportionation catalyst and there is no theoretical upper limit for the amount of magnesium oxide which can be present. Preferred ratios, however, are 0.5 to about 20 parts by weight of magnesium oxide per part by weight of disproportionation catalyst. Equal parts of each catalyst give excellent results.

In a preferred embodiment of the invention, the catalyst bed is configured so that the upstream end of the bed is substantially pure isomerization catalyst and the downstream end of the bed is approximately an equal mixture of isomerization catalyst and disproportionation catalyst, based on weight. At the downstream end, the weight ratio ranges from about 25:75 to 75:25, usually from about 60:40 to about 40:60. The reactor itself is preferably a downflow unit, and the catalyst is layered so that the concentration of disproportionation catalyst increases toward the downstream end of the bed. In other words, the $WO_3:M_gO$ ratio increases from upstream to downstream through the unit. In an embodiment of the invention which has been used with good results, four layers of approximately equal volume formed the reaction zone, and the $M_gO:WO_3$ on silica weight ratio progressed 1:0, 5:1, 3:1 and 1:1 through the unit.

The conversion can be carried out at any convenient pressure up to about 2,000 psig or higher, preferably 0 to 500 psig, typically 400 psig, and at weight hourly space velocities (WHSV) of about 0.01 to about 1,000 w/w/hr., usually in the range of 2.7–11.7 based on $M_gO$ or 10.9–46.8 based on $WO_3$ on silica. The mixed bed process can utilize any suitable contacting technique such as fixed bed reactors, fluidized bed reactors, suspended catalyst systems, and the like, and is effective with both gas phase and liquid phase operation. However, a fixed bed downflow reactor is preferred.

It is preferable to employ tandem reaction zones and to regenerate as needed at temperatures not exceeding 1100 degrees F. with air diluted with nitrogen to about 5% oxygen.

What is claimed is:

1. A process comprising:
   providing a mixed $C_4$ stream comprising butene-1, butene-2, isobutene, butadiene and butanes;
   introducing said mixed $C_4$ stream into an etherification zone;
   reacting at least a portion of said isobutene with an alcohol in said etherification zone to form an ether;
   separating the thus formed ether from the mixed $C_4$ stream to form a deisobutenized stream further containing residual alcohol and ether;
   contacting the deisobutenized stream with a butadiene selective solvent and forming an extract stream containing butadiene and a debutadienized raffinate stream;
   contacting the raffinate stream with an adsorbent material to remove the residual alcohols and ethers and form a deoxygenated stream;
   contacting the deoxygenated stream with a catalyst bed consisting essentially of an olefin isomerization catalyst under conditions to increase the concentration of butene-2 in said stream and to decrease the concentration of butene-1 in said stream and form an isomerizate stream; and
   contacting the isomerizate stream together with ethylene in the presence of a disproportionation catalyst to form propylene.

2. A process as in claim 1 wherein the mixed $C_4$ stream is recovered from thermal cracker effluent;
   wherein the alcohol with which the isobutene is reacted comprises methanol;
   wherein the butadiene selective solvent comprising acetonitrile;
   wherein the adsorbent material with which the raffinate stream is contacted comprises alumina;
   wherein the olefin isomerization catalyst with which the deoxygenated stream is contacted comprises at least 95% by weight of magnesium oxide; and
   wherein the disproportionation catalyst with which the isomerizate stream is contacted comprises a supported tungsten oxide in admixture with an olefin isomerization catalyst.

* * * * *